United States Patent
Herman et al.

(10) Patent No.: US 11,357,955 B2
(45) Date of Patent: Jun. 14, 2022

(54) DEVICES, SYSTEMS, AND RELATED METHODS FOR DELIVERY OF FLUID TO TISSUE

(75) Inventors: Carrie L. Herman, Minnetonka, MN (US); Natalie A. Borgos, Minnetonka, MN (US); Kari L. Cierzan, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1302 days.

(21) Appl. No.: 13/554,176

(22) Filed: Jul. 20, 2012

(65) Prior Publication Data
US 2013/0060229 A1 Mar. 7, 2013

Related U.S. Application Data

(60) Provisional application No. 61/530,080, filed on Sep. 1, 2011.

(51) Int. Cl.
*A61M 25/10* (2013.01)
*A61M 37/00* (2006.01)

(52) U.S. Cl.
CPC .... *A61M 25/1011* (2013.01); *A61M 37/0015* (2013.01); *A61M 2025/105* (2013.01); *A61M 2025/1013* (2013.01); *A61M 2025/1086* (2013.01); *A61M 2037/003* (2013.01); *A61M 2037/0023* (2013.01); *A61M 2037/0046* (2013.01)

(58) Field of Classification Search
CPC ...... A61M 25/1011; A61M 2025/1013; A61M 2025/105; A61M 37/0015; A61M 2037/0023; A61M 2037/003; A61M 2025/1086; A61M 2037/0046
See application file for complete search history.

(56) References Cited

U.S. PATENT DOCUMENTS

| | | | |
|---|---|---|---|
| 2,936,760 A | 5/1960 | Gants | |
| 4,261,339 A | 4/1981 | Hanson et al. | |
| 4,444,188 A | 4/1984 | Bazell et al. | |
| 4,456,011 A | 6/1984 | Warnecke | |

(Continued)

FOREIGN PATENT DOCUMENTS

| | | | |
|---|---|---|---|
| EP | 0363203 A2 | 4/1990 | |
| EP | 0444831 A2 | 9/1991 | |

(Continued)

OTHER PUBLICATIONS

Acconcia, A. et al "Sutureless Vesicourethral Anastomosis in Radical Retropublic Prostatectomy" Am. J. Urol. Rev. Mar./Apr. 2003 1(2): 93-96.

(Continued)

*Primary Examiner* — Emily L Schmidt
(74) *Attorney, Agent, or Firm* — Brake Hughes Bellermann LLP

(57) ABSTRACT

A fluid delivery system including a first balloon and a second balloon at least partially positioned within the first balloon, wherein the second balloon has an inner surface, an outer surface, and at least one micro-needle extending outwardly from the outer surface of the second balloon. The delivery system can further include a fluid source in communication with at least one of the micro-needles of the second balloon.

18 Claims, 5 Drawing Sheets

(56) References Cited

U.S. PATENT DOCUMENTS

| | | | |
|---|---|---|---|
| 4,573,966 | A | 3/1986 | Weikl et al. |
| 4,610,662 | A | 9/1986 | Weikl et al. |
| 4,636,195 | A | 1/1987 | Wolinsky |
| 4,637,396 | A | 1/1987 | Cook |
| 4,660,560 | A | 4/1987 | Klein |
| 4,702,252 | A | 10/1987 | Brooks et al. |
| 4,705,502 | A | 11/1987 | Patel |
| 4,781,677 | A | 11/1988 | Wilcox |
| 4,932,956 | A | 6/1990 | Reddy et al. |
| 4,932,958 | A | 6/1990 | Reddy et al. |
| 5,188,595 | A | 2/1993 | Jacobi |
| 5,312,456 | A * | 5/1994 | Reed .................. A61F 2/82 24/442 |
| 5,344,397 | A | 9/1994 | Heaven et al. |
| 5,549,555 | A | 8/1996 | Sohn |
| 5,707,357 | A | 1/1998 | Mikhail et al. |
| 6,083,166 | A | 7/2000 | Holdaway et al. |
| 6,364,855 | B1 | 4/2002 | Zappala |
| 6,529,011 | B1 | 3/2003 | Piraka |
| 6,638,246 | B1 * | 10/2003 | Naimark .............. A61M 25/10 604/103 |
| 6,719,709 | B2 | 4/2004 | Whalen et al. |
| 6,863,654 | B2 | 3/2005 | Zappala et al. |
| 7,001,405 | B2 | 2/2006 | Kieturakis et al. |
| 7,220,252 | B2 | 5/2007 | Shah |
| 2002/0173745 | A1 * | 11/2002 | Santini, Jr. .............. A23L 2/52 604/67 |
| 2003/0153905 | A1 * | 8/2003 | Edwards ............ A61B 18/1492 606/41 |
| 2004/0087995 | A1 | 5/2004 | Copa et al. |
| 2004/0226556 | A1 * | 11/2004 | Deem ...................... A61M 5/30 128/200.24 |
| 2005/0070938 | A1 | 3/2005 | Copa et al. |
| 2005/0131431 | A1 | 6/2005 | Copa et al. |
| 2006/0058815 | A1 * | 3/2006 | Mickley ............... A61M 25/10 606/118 |
| 2006/0079836 | A1 * | 4/2006 | Holman ............... A61M 25/10 604/96.01 |
| 2006/0206122 | A1 | 9/2006 | Copa et al. |
| 2006/0217680 | A1 * | 9/2006 | Barath ............ A61M 25/0017 604/506 |
| 2006/0264985 | A1 | 11/2006 | Copa et al. |
| 2007/0219584 | A1 | 9/2007 | Copa et al. |
| 2008/0051723 | A1 * | 2/2008 | Laermer ............ A61M 37/0015 604/191 |
| 2011/0166516 | A1 * | 7/2011 | Orr ...................... A61M 25/10 604/103.01 |
| 2013/0331783 | A1 * | 12/2013 | Herman ................ A61M 31/00 604/103.08 |

FOREIGN PATENT DOCUMENTS

| | | |
|---|---|---|
| EP | 0547358 A3 | 6/1993 |
| EP | 1031328 A1 | 2/2000 |
| EP | 1844736 A1 | 10/2007 |
| WO | WO9626748 A2 | 9/1996 |
| WO | WO2004034913 | 4/2004 |

OTHER PUBLICATIONS

Chancellor, M.B. et al. "Inraoperative Endo-Luminal Ultrasound Evaluation of Urethral Diverticula" J. Urol. vol. 153, 72-75 Jan 1995.

Crook, J. et al., "Factors Influencing Rick of Acute Urinary Retention After Trus-Guided . . . ", Int. J. Radiation Oncology Biol. Phys., vol. 52, No. 2, pp. 453-460, 2002.

Diederich, C.J. et al. "Catheter-based Ultrasound Applicators for Selective Thermal Abalation: . . . " Int. J. Hyperthermia vol. 20 No. 7 (Nov. 2004), pp. 739-756.

Igel, C.J., et al, "Comparison of Techniques for Vesicourethral Anastomosis: Simple Direct Versus Modified Vest Traction Sutures" Urol. Jun. 1988 vol. 31 (6) 474-477.

Lee, H.K., et al. "Dosimetric Consequences of Using a Surrogate Urethra to Estimate Urethral . . . ", Int. J. Radiation Oncology Biol. Phys., vol. 57, No. 2. pp. 355-356, 2003.

Merrick G.S., et al, "Phophlactic Versis Therapeutic Alpha-Blockers After Permanent Prostate Brachytherapy," Urology 60 (4), 2002, pp. 650-655.

Ross, A. B. et al, "Highly Directional Transurethral Ultrasound Applicators with Rotational Control for MRI-Guided Prostatic . . . " Phys. Med. Biol. 49 (2004) 189-204.

Ryu, J., et al MRI imaging of the male and female urethra, radiographics. Sep.-Oct. 2001: 21(5): 1169-1185.

Vaidyanathan S., et al., "A Simple Radiological Technique for Demonstration of Incorrect . . . " Scientific Word Jounral. Jun. 20, 2006;6:2445-9.

Zelefsky M., et al "Postimplantation Dosimetric Analysis of Permanent Transperineal . . . " Int. J. Radiaiton Oncology Biol. Phys., vol. 48, No. 2, pp. 60-608, 2000.

Zlotta AR, et al, "Percutaneous Transperineal Radiofrequency Ablation of Prostate Tumor: Safety, Feasilibty and . . . " Br. J. Urol. Feb. 1998, 81 (2); 265-275.

* cited by examiner

DEVICES, SYSTEMS, AND RELATED METHODS FOR DELIVERY OF FLUID TO TISSUE

CROSS REFERENCE TO RELATED APPLICATION

This application claims the benefit under 35 U.S.C. § 119(e) of U.S. Provisional Patent Application No. 61/530,080, filed Sep. 1, 2011 and titled "Devices, Systems, and Related Methods for Delivery of Fluid to Tissue", which is incorporated herein by reference in its entirety.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract (e.g., bladder) of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example.

Needleless fluid delivery systems can include the use of a tube-like device, such as an elongated catheter tube, which is configured to provide a jet-injection of a therapeutic fluid at a desired treatment site. Generally, a needleless injector is used to deliver a therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the fluid to a relatively high pressure in order to achieve a certain desired fluid delivery pressure at the distal end of the device. Needleless devices and methods for treating tissue of the urinary tract are discussed, for example, in U.S. Patent Application Publication No. 2009/0312696 (Copa et al.), and U.S. Patent Application Publication No. 2006/0129125 (Copa et al.), the entire disclosures of which are incorporated herein by reference.

One particular application for needleless fluid delivery systems is for treatment of diseases of the prostate, such as prostatitis, benign prostatic hyperplasia, and prostatic carcinoma. In addition to prostate treatments, tissue of the urinary tract can be affected by medical conditions that can be treated by delivery of various therapeutic materials in the form of fluids. Tissues of the bladder (which includes the bladder neck), ureter, kidneys, urethra, as well as the prostate, can be treated by delivery of drugs or other therapeutic agents. Various treatments of the bladder, such as transurethral administration of an active pharmaceutical agent, involve placement of a therapeutic fluid into the bladder using a single needle located at the distal end of a rigid shaft inserted into the bladder through the urethra. However, practical challenges exist for performing injections of bladder tissues, which can be thin in their depth dimension (i.e., shallow), making injection a challenge. For these tissues, there is ongoing need to improve injections, such as by increasing uniform distribution of agents within the thin tissue, over a desired area of the tissue.

For any injection or injected tissue, therapeutic agents are desirably delivered with minimal discomfort and procedure time, with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery. Such procedures, systems, and components can provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention involves fluid injection devices that use balloons and/or micro-needles. These devices allow for localized delivery of therapeutic fluids that include biologically active species and agents such as chemical and biochemical agents, at desired anatomical tissue locations including but not limited to locations in the male or female urinary tract, e.g., bladder, bladder neck, kidney, ureters, urethra, prostate, etc. Exemplary devices are capable of delivering fluid at various tissue locations, and can optionally also deliver multiple different therapeutic fluids at one or more tissue locations, either simultaneously or sequentially. These devices are capable of delivering precise amounts of fluid for injection at one or more predetermined locations, which provides for improved treatment due to the precision and accuracy of the fluid delivery. In one particular embodiment, fluids such as the fluid commercially available under the trade name "Botox", or other drug therapy fluids, can be delivered to the inner lining of the bladder, such as for the treatment of overactive bladders or other incontinence conditions.

Features of described devices and methods address certain practical problems associated with delivering and/or injecting fluid into tissue. For example, injection of fluid into bladder tissue by use of a single needle at a distal end of a rigid shaft typically requires specialized dexterity and skills of a doctor due to the somewhat cumbersome nature of a rigid shaft that has just one distal needle. Devices and methods described herein overcome some of the challenges involved in using other available tissue injection methods.

In one embodiment of the invention, devices and/or methods are used to deliver material (e.g., drug delivery fluids, Botox, and the like) to one or more locations in the bladder of a patient without the use of incisions. With such devices and/or methods, one or more micro-needles are associated with an internal balloon. This internal balloon is positioned within an external balloon, wherein the micro-needles of the internal balloon are initially spaced from the inner surface of the external balloon, which helps to protect the inner lining of the bladder and other adjacent tissues from the micro-needle tips during placement of the devices within the bladder. After placement in a desired location, the outer balloon can be expanded to inflate or expand the bladder by a desired amount, and then the inner balloon can be inflated so that the micro-needles pierce through the outer balloon. Fluid can then be delivered or injected into the bladder tissue through the micro-needles to provide a desired tissue treatment.

In another embodiment, the bladder is first drained by inserting a balloon into the bladder, then inflating the balloon to force fluid from the bladder into a catheter-type tube. The balloon of this embodiment may also include outwardly extending micro-needles. Inflation of this balloon allows for direct contact between the balloon and the inner surface of the bladder, which in turn allows for penetration of the micro-needles into the desired tissue for injection of fluids. The micro-needles can be provided with a number of different configurations that allow for accurate fluid delivery without damaging the tissue that it penetrates.

In yet another embodiment, a bladder balloon system with micro-needles is used to deliver cells, Botox, or drug delivery materials to bladder tissue in which the system includes a lining that absorbs and/or degrades when it comes in contact with liquids. After such a degradation of the lining, the micro-needles will be exposed so that the therapeutic fluid can be delivered into the target tissue.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
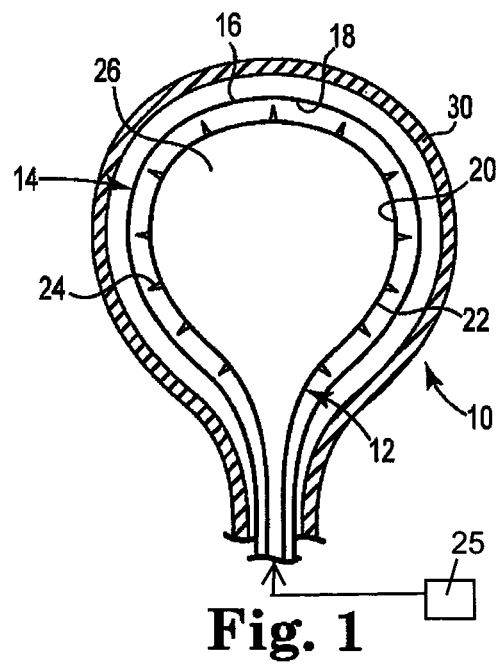
FIG. 1 is a cross-sectional front view of a bladder into which an embodiment of a fluid injection device of the invention has been positioned.

The invention relates to devices and methods useful for injecting fluid into tissue for treatment. For example, the devices and methods can be useful for delivering fluids such as the fluid commercially available under the trade name "Botox", cells, or other drug therapy fluids, to the inner lining of the bladder, such as for the treatment of overactive bladder conditions or other incontinence conditions. Such concepts can be used to allow drugs or Botox to be delivered to multiple points within the bladder at a single time and can deliver these materials without requiring any incision(s). The injectable materials can be delivered or injected using micro-needles, which are selected from materials that are safe for implantation and/or short-term tissue contact within the patient. Similarly, any balloons or balloon-like components that are used should be made from materials that are safe for short-term tissue contact.

The micro-needle systems of the invention can include one or more orifices that deliver fluid in the form of a jet or fluid stream that is injected into relatively thin tissue without adversely damaging that tissue. This fluid is delivered at a pressure, velocity, and stream size that allow the fluid stream to pass through a tissue surface, penetrate into the bulk of the tissue below the tissue surface, and become dispersed within the tissue. The type of tissue injected for treatment can be any amenable tissue, such as tissue at or near the urinary tract (e.g., tissue of the prostate, kidneys, ureters, urethral tissue, bladder, or other tissues such as heart tissue).

The balloon delivery systems described herein generally include a distal end and a proximal end. As used herein, a "distal end" of a device or system generally refers to an end area or portion of the device or system that can be introduced into a patient's body during a treatment procedure. For example, elongate shafts or catheters of the delivery systems of the invention can include a distal end, which is typically one of the first portions of the device to be inserted into the patient for treatment. The distal end may include functional features that operate on fluid or tissue during use, such as micro-needles and balloons, for example.

As used herein, a "proximal end" of an exemplary system of the invention is the end that is generally opposite the distal end of that device or system. It is noted that each individual component of a system can include its own proximal and distal ends, while the overall system can also include proximal and distal ends. For one example, a micro-needle and balloon system of the invention can include an injector body or console at a proximal end that remains external to the patient during use and an elongate shaft or catheter tube at a distal end. One or more micro-needles at the distal end can be in fluid communication with the console. The console can further include a user interface that has a means for selectively delivering a volume of fluid to one or more balloons, micro-needles, or other system components. The user interface can include one or more controllable devices, such as foot pedals, hand-activated controllers, switches, buttons, and/or the like. It is also contemplated that the user interface can include a touchscreen that is capable of receiving touch commands. The user interface can also optionally include a display system for displaying information such as the mode of operation that is being used and/or certain operating parameters of the system.

An exemplary console used with systems of the invention can include a housing that connects to or is otherwise (directly or indirectly) in fluid communication with an elongate shaft or catheter tube. The console can include fluid that is pressurized by a pressure source to cause the fluid to flow through the shaft for injection into tissue at the distal end. The device can eject fluid from one or more micro-needles that are located at the distal end of its shaft or catheter tube. A console can have any configuration, size, or design, ranging from a small, hand-held design to a relatively large floor or table-mounted console. The console can also include separate or separable components such as a pressure chamber or injection chamber that can be attached, used for an injection procedure, and detached and then optionally discarded or sterilized and reused. A shaft or catheter tube can also be attached to a console or a pressure chamber in a manner that facilitates separation and optional re-attachment, replacement, and/or disposal.

The balloons described herein relative to the fluid delivery systems of the invention can be formed from a suitable elastomeric material such as natural rubber, synthetic rubber, including styrene-butadiene copolymers, polyisoprene, isobutylene-isoprene copolymers (butyl rubber), including halogenated butyl rubber, butadiene-styrene-acrylonitrile copolymers, silicone and fluorosilicone elastomers, polyvinylchloride, polyester, or polyurethane, and polyamides. Combinations of more than one elastomeric material can be used to make the balloon. Multi-layered balloon constructions can also be used. Exemplary multi-layered balloon constructions are described in various references such as U.S. Pat. No. 4,637,396 which describes a three layer wall, and in U.S. Pat. No. 4,651,721. Many manufacturing processes for balloon construction involve molding of thermoplastic material. For example, thermoplastic material can be expanded in association with a mold to provide a balloon that in its inflated configuration has the shape of the inside of a bladder.

The balloons used with the fluid delivery systems described herein can be constructed to have a cross-sectional thickness of the elastic material that is appropriate for the therapeutic agent delivery method and apparatus. The thickness refers to the elastic balloon material and does not take into consideration the length of the micro-needles that are attached to the outer surface of the balloon. The cross-sectional thickness of the elastic material can vary based on factors such as the balloon's pressure ranking, expansion attributes, and pliability.

Any of the fluids that are injected into tissue using systems of the invention may be referred to as an "injectate" or "injection fluid", which may be any type of fluid such as a therapeutic fluid. Exemplary balloons used for the invention can deliver a certain quantity of injectate (e.g., at least 30 milliliters of fluids, such as Botox) with a single application. When micro-needles are used for the fluid delivery, exemplary needles can have an inner diameter of at least 27 gauge (i.e., a nominal 0.00825 inches (0.210 mm)), although needles having a larger or smaller inner diameter can be used. With regard to other uses of needles, see for example, *Technology Review Tiny Needles to Fight Cancer*, MIT, Sep. 1, 2010; and Harper et al., *Points of Technique*, BJU International 92 (2003): 325-326.

Referring now to the Figures, a number of exemplary embodiments of fluid injection systems of the invention are illustrated, which generally include one or more balloons and/or micro-needles for delivering, positioning, and injecting fluid into target tissue. It is noted that although much of the description herein refers to and illustrates use of the fluid injection systems in a bladder, it is understood that the systems can instead be used for injecting fluid into other areas of the body that can be accessed with these injection systems.

Figure 2:
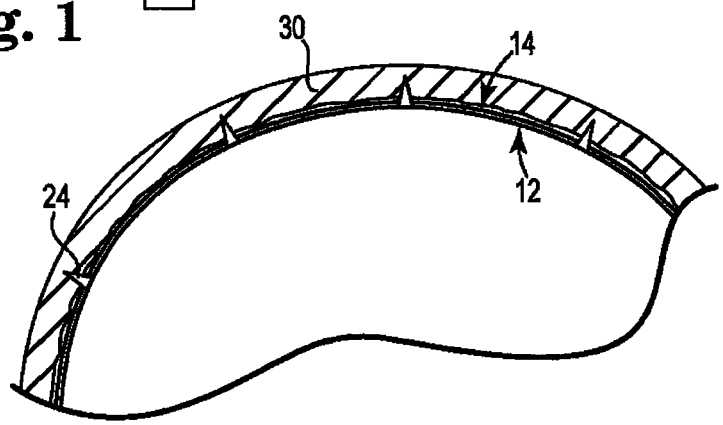
FIG. 2 is an enlarged cross-sectional front view of a portion of the fluid injection device illustrated in FIG. 1.

FIGS. 1 and 2 are schematic views of a fluid injection system 10 that includes a first or inner balloon 12 positioned within a second or outer balloon 14. FIG. 1 illustrates a configuration prior to expansion of the balloons 12, 14 and FIG. 2 illustrates a configuration in which the balloons 12, 14 have been expanded for fluid injection into tissue. The outer balloon 14 includes an outer surface 16 and an inner surface 18, both of which can be generally smooth or at least slightly textured. The outer balloon 14 further includes a thickness between the inner and outer surfaces 16, 18. The outer balloon 14 is structured so that its outer surface 16 will contact the inner walls of the area in which it is placed in the body (e.g., the inner wall of a bladder) when it is inflated. Inner balloon 12 includes an inner surface 20 and an outer surface 22 from which multiple micro-needles 24 outwardly extend. Each of these micro-needles 24 includes an inner lumen (not visible) that extends from its distal end to its proximal end and through the thickness of the material that makes up the inner balloon 12. In this way, fluid that is added to an inner area 26 of the first or inner balloon 12 from a fluid source 25 will be moveable from the inner area 26, through the thickness of the inner balloon 12, and through the inner lumen of each of the micro-needles 24 to their distal ends.

In operation, the dual-balloon system 10 can be inserted into a bladder 30 or other structure of a patient in an uninflated or semi-inflated condition, as is illustrated in FIG. 1. After insertion, the outer balloon 14 is inflated until its outer surface 16 contacts the inner wall of the bladder 30, and then is further inflated to cause expansion of the bladder 30 to a desired size. After this outer balloon inflation is complete, the inner balloon 12 is inflated until its outer surface 22 is closer to the inner surface 18 of the outer balloon 14 and extending micro-needles 24 come in contact with the inner surface 18 of the outer balloon 14. Further inflation of the inner balloon 12 will cause the micro-needles 24 to pierce through the thickness of the outer balloon 14 and into the tissue of the bladder wall by a desired depth, as is illustrated in FIG. 2. After the micro-needles 24 are in their desired position, a therapeutic quantity of a treatment fluid or cells can be added to the inner area 26 of the inner balloon 12 under high enough pressure that it will move into and through the micro-needles 24, and then exit the distal end of the micro-needles 24 into the bladder tissue. In this way, fluid will be injected into the tissue that is penetrated by the micro-needles 24.

The dual-balloon configuration of the system 10 can be preassembled outside the patient's body so that the inner balloon 12 is positioned within the outer balloon 14 prior to insertion of the system 10 into the patient (i.e., both balloons 12, 14 are inserted into the patient as a single unit or system). Alternatively, the outer balloon 14 can be inserted into the patient first, after which the inner balloon 12 can be inserted into the outer balloon 14. With either of these configurations, the outer balloon 14 advantageously prevents or minimizes unintentional contact between the micro-needles 24 and the bladder tissue and/or any surrounding tissue that would be encountered by the micro-needles 24 along the path to the bladder. Thus, the material from which the outer balloon 14 is made is preferably sufficiently resistant to being punctured by the needles 24 when only minimal or incidental contact between needles 24 and the outer balloon 14 occur, but should be able to be punctured by the micro-needles 24 with a reasonable amount of force or pressure when the inner balloon 12 is inflated.

The micro-needles 24 can be selected and/or designed to have a size and shape that allows for penetration of the outer balloon 14 and a predetermined amount of penetration into the adjacent tissue. That is, the micro-needles are preferably long enough to be able to extend through the material thickness of the outer balloon 14 and into the tissue by a desired distance, but not so long that they can cause unintentional damage to the tissue being penetrated and/or any other surrounding structures. The distal ends of the micro-needles 24 can have a wide variety of shapes and sizes, with one exemplary configuration being a needle that tapers in size from its proximal end to its distal end so that its distal end is sufficiently sharp that it can penetrate the balloon and tissue.

Figure 3:
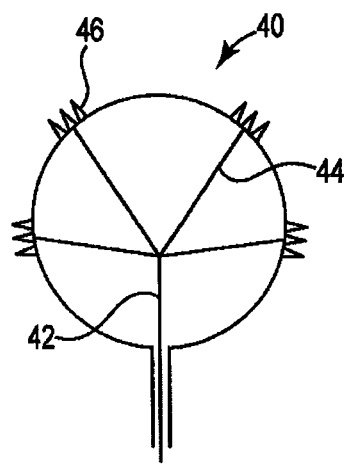
FIG. 3 is a cross-sectional front view of a fluid injection device of the invention.

FIG. 3 illustrates an exemplary embodiment of another device 40 for supplying fluid to micro-needles in a system that is similar to the embodiment illustrated in FIGS. 1 and 2. The device 40 is a balloon structure that cooperates with a central supply line 42 that divides or branches into several smaller supply lines 44, each of which extends to at least one micro-needle 46. In this embodiment, a sufficient amount of pressure is generated in the supply lines 44 that provide fluid to the micro-needles 46 to push fluid through the micro-needles 46 and into tissue of a patient. As shown in this embodiment, each smaller supply line 44 is associated with three micro-needles 46 that are grouped together, although the number of micro-needles 46 and supply lines 44 can vary from the illustrated embodiment.

In a variation of the invention, a third balloon is provided that is positionable within a second or inner balloon of a system that also includes a first or outer balloon, such as the inner and outer balloons 12, 14 described above. In this embodiment, the third balloon would be provided to further assist in pushing fluid into and through the micro-needles under pressure.

Figure 4:
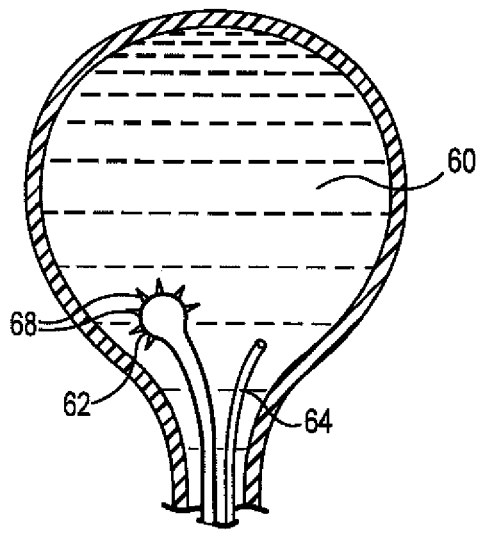
FIG. 4 is a cross-sectional front view of a bladder into which an embodiment of a fluid injection device of the invention has been positioned in its deflated state.
Figure 5:
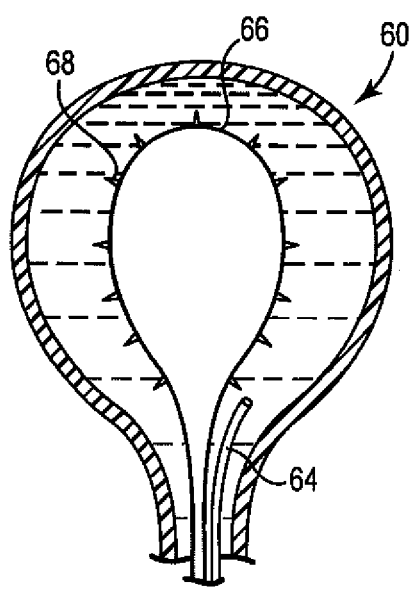
FIG. 5 is a cross-sectional front view of the bladder and fluid injection device illustrated in FIG. 4, with the injection device in a semi-inflated state.
Figure 6:
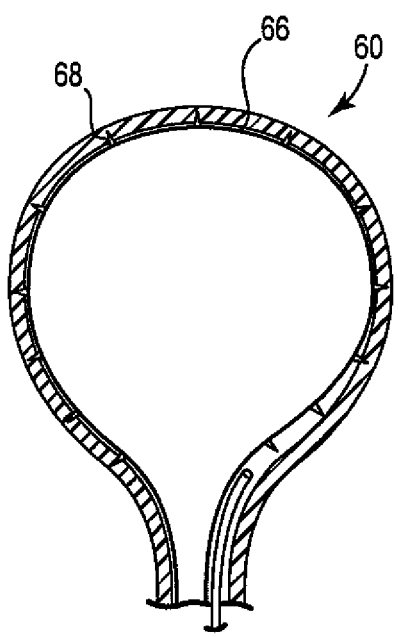
FIG. 6 is a cross-sectional front view of the bladder and fluid injection device illustrated in FIGS. 4 and 5, with the injection device in an inflated state.

FIGS. 4-6 illustrate another embodiment of a fluid delivery system 60 that includes balloons with micro-needles. In one exemplary use of this system 60, stem cells or therapeutic fluids can be delivered to multiple areas of a bladder simultaneously, such as for the treatment of overactive bladder. Fluid delivery system 60 includes a balloon 62 and an associated catheter 64. The catheter 64 can also function as a delivery system to move the balloon 62 to its desired location in the patient. The balloon 62 includes an outer surface 66 from which at least one micro-needle 68 extends in an outward direction. The balloon 62 and catheter 64 can be operatively connected so that they can function as a single system, or can instead be inserted separately into the patient. In one embodiment, the balloon 62 and catheter 64 are attached to each other along at least a portion of their lengths so that they can be positioned in a desired orientation relative to each other when inserted into a target location in the patient.

FIG. 4 illustrates an exemplary situation in which the catheter 64 and the deflated balloon 62 are being inserted into a bladder through a urethra when the bladder is at least partially filled with fluid. The catheter 64 can be used to assist in positioning the balloon 62 in a desired location relative to the bladder so that when the balloon 62 is inflated, fluid will be pushed from the bladder into an inner lumen of the catheter 64, thereby draining the bladder. FIG. 5 shows the balloon 62 in a partially inflated condition in which some of the fluid has been drained from the bladder through the catheter 64. The balloon 62 is then further inflated until it contacts the inner bladder wall, thereby completely emptying fluid from the bladder, as is illustrated in FIG. 6. Because the balloon 62 of this embodiment includes micro-needles 68 extending from its outer surface 66, a certain amount of inflation of this balloon 62 will also cause the micro-needles to penetrate the inner bladder wall. This balloon inflation advantageously conforms to the inner shape of the bladder through direct contact with the inner wall of the bladder. Once the micro-needles are in place, fluid, stem cells, or other material can be provided to the outer balloon so that it is delivered to tissue through the micro-needles.

Figure 7:
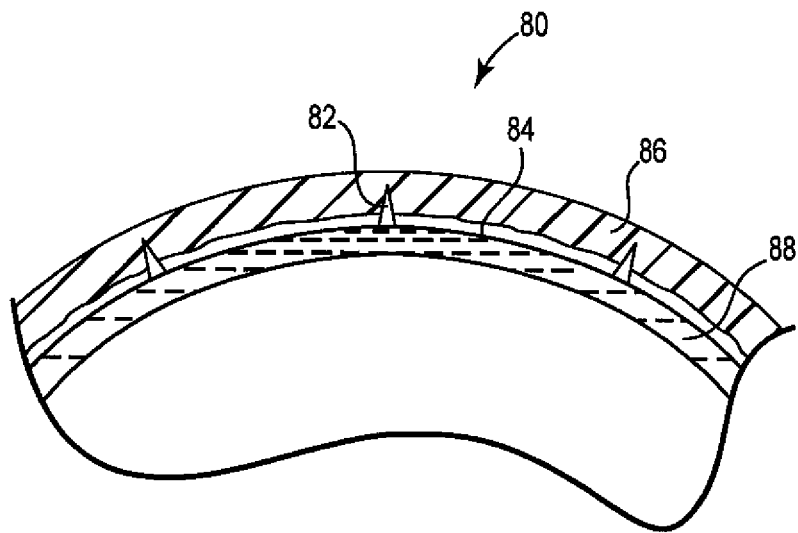
FIG. 7 is an enlarged cross-sectional front view of a portion of a fluid injection device of the invention, including multiple needles penetrating adjacent tissue.

Another exemplary configuration of a balloon structure 80 is illustrated in FIG. 7, which includes micro-needles 82 extending from an outer balloon 84 and into adjacent tissue 86. As shown, the outer balloon 84 is spaced from an inner balloon by a space 88. In operation, the outer balloon 84 does not contain fluid until the inner balloon is fully inflated, and then the fluid can be injected into the outer balloon 84. In this way, fluid can be added under pressure into the space 88 between the two balloon walls to supply fluid to the micro-needles 82.

Figure 8:
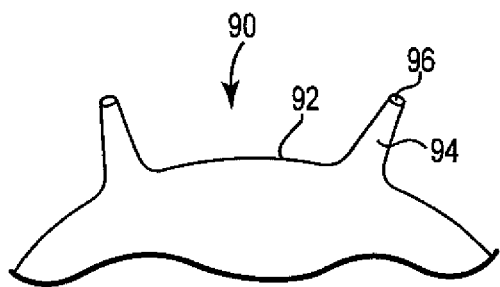
FIG. 8 is a front view of a portion of a balloon member of a fluid injection device, including exemplary micro-needles extending from its outer surface.

FIG. 8 illustrates a portion of an outer surface of an exemplary balloon 90 that can be used in accordance with systems of the invention. As shown, the balloon 90 includes an outer surface 92 from which multiple micro-needles 94 extend, each of which includes a hollow interior lumen that terminates in a needle tip opening 96. The micro-needles allow for the movement of material from the inner area of the balloon 90 to the tip openings 96 at the distal ends of the micro-needles 94. Such a configuration can help to provide controlled movement of material through the micro-needles 94 until the needles are properly positioned relative to the tissue (e.g., bladder tissue) into which the material will be injected.

Figure 9:
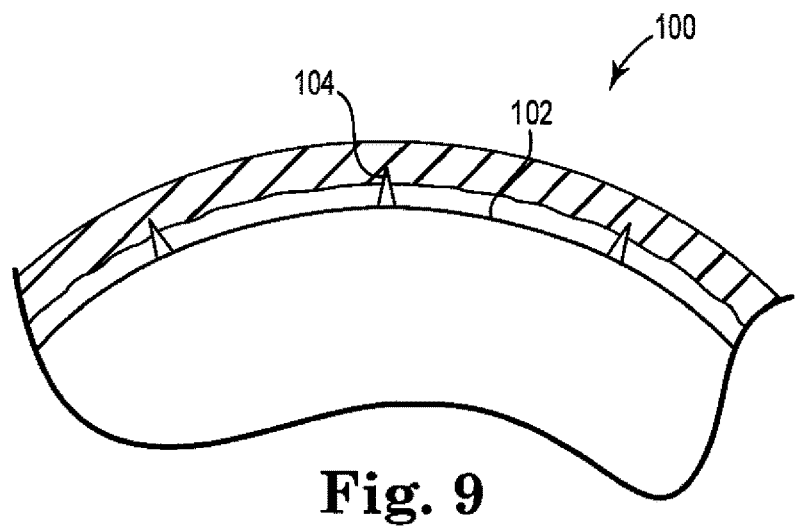
FIG. 9 is an enlarged cross-sectional front view of a portion of a fluid injection device of the invention, including multiple needles penetrating adjacent tissue.

Another exemplary balloon system 100 with micro-needles 104 is illustrated in FIG. 9. System 100 includes a single balloon that has micro-needles 104 extending outwardly from its outer surface 102. With such an embodiment, the balloon can be positioned within the patient, after which it can be inflated until the needles penetrate the adjacent tissue. The inner volume of the balloon can be filled with stem cells and/or accompanying fluids for movement of such materials through the micro-needles 104 and into the adjacent bladder tissue.

Figure 10:
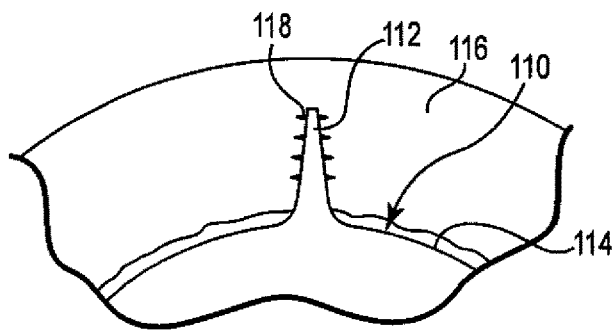
FIG. 10 is an enlarged cross-sectional front view of a portion of a fluid injection device of the invention, including one needle having a textured outer surface that is penetrating adjacent tissue.
Figure 11:
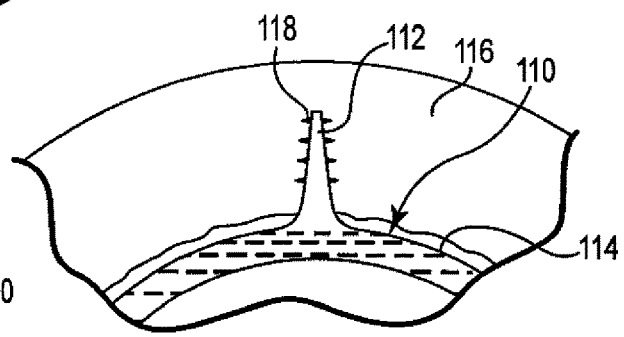
FIG. 11 is an enlarged cross-sectional front view of a portion of the fluid injection device illustrated in FIG. 10, including one needle separated from the balloon and positioned within tissue.

FIGS. 10 and 11 illustrate a portion of another exemplary balloon 110 of a fluid delivery system of the invention, which includes micro-needles 112 that are initially extending outwardly from its outer surface 114 (see FIG. 10). The micro-needles 112 are themselves made of the material that is desired to be inserted into the surrounding bladder tissue and/or other tissue 116. That is, any or all of the micro-needles 112 can be made from stem cells or some other material that are in such a state that they are absorbable or partially absorbable into tissue with which they come into contact. In other words, the micro-needles themselves can be considered to be bioabsorbable elements of the balloon 110 such that the micro-needles 112 can be separated from the balloon surface and remain in the tissue to be absorbed therein. Such absorption can either occur somewhat rapidly or can take place over a predetermined length of time. The separation of the micro-needles from the balloon 110 can be facilitated by burrs or other texturized features 118 on the outer surface of the micro-needles 112. These texturized features 118 provide for a more secure contact between the outer surface of the micro-needles 112 and the surfaces that they are penetrating than the contact or attachment between the micro-needles 112 and the outer surface 114 of the balloon 110. In this way, the needles will break from the balloon 110 and remain lodged in the tissue as the balloon 110 is deflated, as is illustrated in FIG. 11.

In another variation of the balloon of FIGS. 10 and 11, the amount of material to be inserted into the tissue 116 can be controlled by the amount of time that the balloon 110 remains inflated with the micro-needles 112 penetrating the tissue. In such a case, when it has been determined that the needles have been in place long enough to provide a desired amount of material to the tissue via the micro-needles 112, the balloon 110 can be deflated to remove the pressure that is pushing the micro-needles 112 into the tissue. In this embodiment, the connections between the needles 112 and the outer surface 114 of the balloon 110 are relatively strong such that any portion of the micro-needles 112 that are not absorbed by the tissue will be remain attached to the balloon 110 as it is deflated, thereby removing the needles from the tissue.

Figure 12:
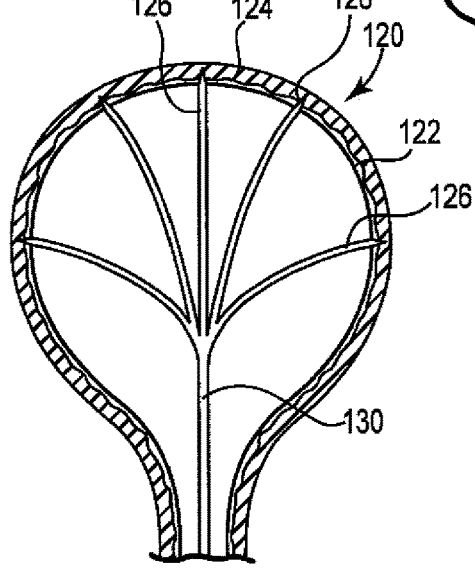
FIG. 12 is a cross-sectional front view of a bladder into which an embodiment of a fluid injection device of the invention has been positioned.

Another exemplary balloon system 120 is illustrated in FIG. 12, which includes an outer balloon 122 that is inflatable or expandable for draining fluid from the bladder and for pressing against the inner bladder wall 124. This system 120 further includes one or more relatively flexible tubes or leads 126 that extend through the interior area of the balloon 122 to the surface of the balloon 122 where each of the tubes 126 terminates in one or more micro-needles 128. The needles 128 can then facilitate delivery of material into the bladder tissue. The tubes 126 can therefore be considered to be configured as micro-needles that are positioned in desired locations to treat the bladder. Therapeutic fluids, Botox, or cells (e.g., stem cells) can be delivered through these micro-needles 128 to achieve a desired result. Although the tubes 126 with micro-needles 128 are illustrated in a "fan-like" configuration in this figure, it is understood that these tubes 126 can be arranged in any configuration that allows the tubes 126 to reach the desired areas of the patient, such as the bladder. It is further understood that although this embodiment illustrates one main supply line 130 that branches into multiply supply tubes 126, one or more main supply tubes or lines can be provided, each of which includes any number of individual delivery tubes 126 extending therefrom.

In accordance with embodiments of the invention, in order to deliver fluid into an outer bladder balloon and then through any micro-needles that are provided, the balloon system can be designed and built so that when fluid is introduced into the outer balloon, an inner balloon is slowly deflated. Releasing the pressure in the inner balloon will decrease the force that the fluid will need to overcome when entering the outer balloon and micro-needles.

Figure 13:
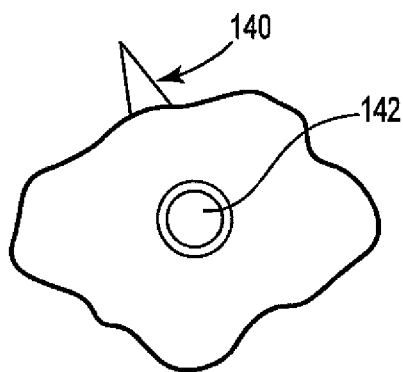
FIG. 13 is a bottom perspective view of a needle structure of a fluid injection device of the invention.
Figure 14:
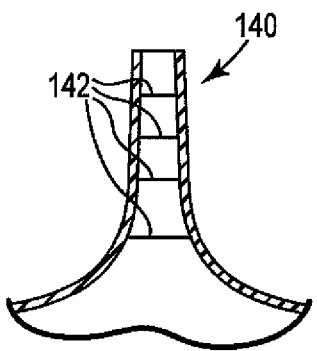
FIG. 14 is a cross-sectional side view of a needle structure of a fluid injection device of the invention.

FIGS. 13 and 14 illustrate yet another exemplary embodiment of a portion of a delivery system that uses at least one balloon having extending micro-needles for delivering fluid or other materials to tissue. With this embodiment, a balloon is used that has an aperture through its surface from which each micro-needle 140 extends. The balloon further includes at least one absorbable/biodegradable film or layer 142 that covers or partially covers some or all of its apertures adjacent to a surface of the balloon. Such a film or layer 142 can be located to be flush with the inner surface of the balloon, to be flush with the outer surface of the balloon, or to be flush with both the inner and outer balloon surfaces. The film or layer(s) 142 can alternatively or additionally be positioned at any desired location along the length of the micro-needle 140, with four exemplary locations for the film or layer 142 being illustrated in FIG. 14. With any of the film locations, the balloon can initially be inflated with a liquid, such as stem cells, therapeutic fluids, saline, or the like, and when the film or layer is contacted by such materials, it can degrade in such a way that the apertures are at least partially open. In this way, fluid will be allowed to pass through them and into the bladder tissue or other patient tissue. Alternatively or additionally, a film layer can be positioned at one or more points along the length of one or more micro-needles in order to provide such an initial blockage of fluid through the micro-needles. These film layers can similarly degrade to allow fluid or other materials to flow through the micro-needles.

Figure 15:
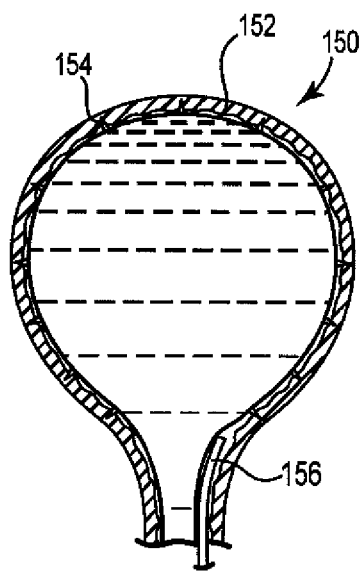
FIG. 15 is a cross-sectional front view of a bladder into which an embodiment of a fluid injection device and catheter of the invention has been positioned.

FIG. 15 is an illustration of another balloon system 150 that includes a balloon 152 with micro-needles 154 extending from its outer surface, along with a catheter 156. In this embodiment, the balloon 152 is fully inflated against the target tissue (e.g., a bladder wall) prior to the introduction of therapeutic fluid into the inner volume of the balloon. The needles 154 allow for introduction of a liquid solution, such as might include stem cells, Botox, therapeutic materials, and the like, after the balloon is fully inflated and pressing against the wall of the bladder or other organ into which it is inserted and deployed.

Figure 16:
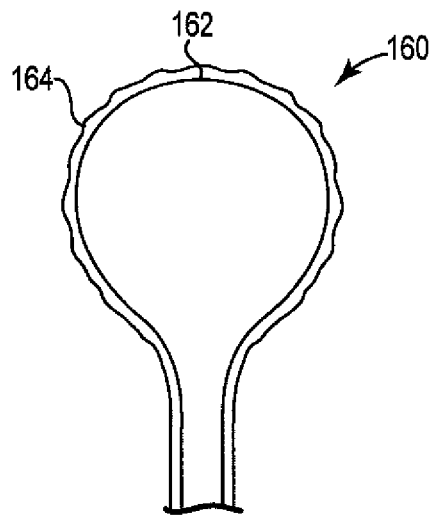
FIG. 16 is a cross-sectional front view of a bladder into which an embodiment of a fluid injection device of the invention has been positioned.
Figure 17:
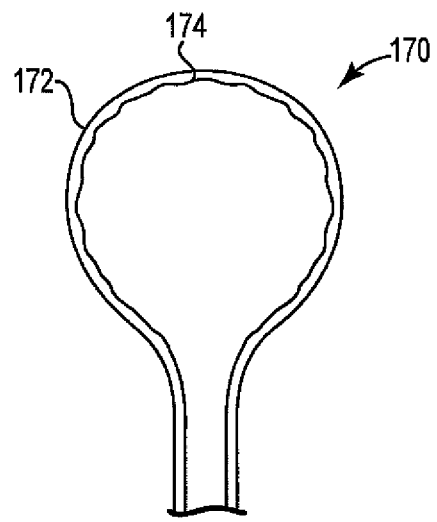
FIG. 17 is a cross-sectional front view of a bladder into which an embodiment of a fluid injection device of the invention has been positioned.

FIGS. 16 and 17 illustrate additional exemplary fluid delivery systems 160, 170 that include multiple balloons, which are provided for use in an organ such as the bladder. With these systems, at least one of the balloons is provided with a non-smooth surface to make it easier to establish a space between the outer surface of the inner balloon and the inner surface of the outer balloon when the inner balloon is expanded and pressed against the outer balloon. Such a space between the balloon surfaces may be desirable for injection of fluids or other materials between the balloons, for example. Delivery system 160 of FIG. 16 is illustrated with an inner balloon 162 having smooth surfaces positioned within an outer balloon 164 that has textured inner and outer surfaces. Delivery system 170 of FIG. 17 is illustrated with an outer balloon 172 having smooth inner and outer surfaces and an inner balloon 174 positioned therein that has textured inner and outer surfaces. In other alternatives of the systems 160, 170, the balloons that have textured inner and outer surfaces may be provided with only one textured surface, rather than both. As shown, the textured surfaces of one of the balloons can provide for a space between the balloons to allow material to be positioned between the balloons and distributed throughout that space. However, the textured or patterned balloon can also be inflatable to a further-expanded state in which the textured surface will be "tightened" or "smoothed" out so that it can come into closer contact with an adjacent balloon and eliminate the spaces between the two balloons. In this way, all of the cells or fluid between the balloons can be pushed out of the balloon, when desired.

Because there may be areas within the delivery systems of the invention where cells and/or fluids can remain (e.g., delivery lines, balloons, etc.), it is generally desirable for the systems to be configured so that as much of the cells and/or fluids can be pushed through and delivered to the tissue/ organs as possible. After the cells and/or fluids have been pushed into the delivery system, saline can be injected into the system. The saline can thereby be used as a medium to further push any remaining cells and/or fluids through the system. As an added benefit, any saline that comes into contact with the bladder can cause a minor amount of irritation, which in turn can cause any injected cells to work more quickly, and would also help to keep the cells in place.

Although some of the features of the fluid delivery systems are discussed herein with particular reference to certain embodiments, it is understood that features of the embodiments described herein can be combined with features of other embodiments to provide additional fluid delivery systems that are considered to be within the scope of the invention.

In order to provide short-term pelvic support until adequate native tissue support is re-established (e.g., collagen, elastin, muscle, and other tissue regeneration), silk grafts with cells (e.g., stem cells) can be used, which can be injected or delivered to an inner lining of a bladder or other location in a patient via any of the micro-needles, balloons, or other devices and methods described herein, for example. The use of stem cells, such as adipose-derived stem cells and compositions, for treatment of various pelvic floor conditions using other delivery methods and devices is described, for example, in PCT International Publication No. WO 2009/120879 A1, the content of which is incorporated herein in its entirety. These silk grafts can be used in any area of the pelvic floor to encourage tissue healing and support, and to prevent or reduce adhesions following invasive procedures, such as procedures that are used to address issues such as prolapse, fecal incontinence, and stress urinary incontinence. The use of stem cells can help to stimulate growth and healing, while the silk graft can provide short term organ and/or tissue support and can provide a scaffold for stem cells and tissue in-growth. Further, because the silk graft will become absorbed over time, no permanent implant will be left behind in the patient.

In one mode of practice, adipose-derived cells (ADCs) are removed from adipose tissue and introduced to the treatment region following the use of collagenase to break apart the connective tissue. Adipose (i.e., fat) tissue includes or yields a high number of desirable cell types, including stem cells. The adipose tissue can come from anywhere in the body. In one embodiment, the adipose tissue is obtained from the abdominal area of the patient. Other common areas may include the thigh and back area of the patient. If desired, a portion of the adipose tissue is set aside for preparing a "cell matrix" which can be remixed with an enriched population of cells from the adipose tissue.

In some modes of practice, adipose tissue is processed to separate the adipose-derived stem cells from the other material including other cellular and non-cellular material in the adipose tissue. Preparation methods can include steps of washing the tissue, treating the tissue with collagenase or trypsin, or optionally with mechanical agitation. Liposomes, which are generally aggregated, can be separated from free stromal cells which include the stem cells and other cells such as red blood cells endothelial cells, and fibroblast cells, by centrifugation. Erythrocytes can be lysed from the suspended pellet and the remaining cells can be filtered or centrifuged. Optionally, cells may be separated by cell sorting or separated immunohistochemically. Methods for the preparation of adipose-derived stem cells are described in commonly-assigned PCT International Publication No. WO 2009/120879. In other modes of practice, the adipose tissue is processed to remove partially or substantially non-cellular components, and to form a heterogenous cell mixture. The heterogenous cell mixture can include endothelial cells, endothelial precursors and progenitors, mesenchymal stem cells, vascular smooth muscle cells, fibroblasts, pericytes, macrophages, and the like.

In some modes of practice, the cell matrix is prepared from a portion of the adipose tissue obtained from the patient. To prepare the cell matrix, the adipose tissue can be disaggregated by mechanical force, such as by cutting, chopping, or mincing the adipose tissue. Generally, for this cell matrix preparation, collagenase or trypsin (enzymatic) digestion is not performed to maintain the scaffolding features of the adipose tissue. The adipose particles generated using such a process are sized for penetration into the penile tissue. Grinding and filtering parameters can also be employed depending on the particular treatment site needs. The cell-containing composition can also include an amount of solids material that are not cells derived from the adipose tissue. For example, this solids material can include cell matrix material such as natural or synthetic polymeric material, material from PRP or PPP, or cell scaffolding derived from mechanically processed adipose tissue.

Although grafts are described above as being silk with cells, it is understood that different and/or additional biodegradable materials could instead be used, wherein all of the materials are selected or designed to be safe for implantation within a patient. The grafts can be made in various sizes, shapes, and configurations, depending on the application and the size and shape of the area where the application is desired. With regard to the use of silk materials, see for example, Zou et al, *Mesenchymal stem cell seeded knitted sling for the treatment of stress urinary incontinence*, Biomaterials 31 (2010); 4872-4879; and Kundu et al., *Osteogenesis of human stem cells in silk biomaterial for regenerative therapy*, Prog Polym Sci (2010); doi:10.1016/j.progpolymsci.2010.04.004.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but is also intended to encompass equivalents of those structures.

The invention claimed is:
1. A system for delivering a therapeutic material to a target tissue of a patient, the system comprising:
   a first expandable balloon including an outer surface, the outer surface configured to contact the target tissue within a pelvic region of the patient;
   a second expandable balloon at least partially positioned within the first balloon and separately inflatable from the first balloon, the second balloon including an inner surface, an outer surface, and a plurality of micro-needles disposed on the outer surface of the second balloon and extending outwardly from the outer surface of the second balloon, each of the plurality of micro-needles including:
a proximal end;
a distal end; and
an inner lumen extending from the proximal end to the distal end;
a main supply tube that extends into the second balloon having a first end;
a first supply tube having a first end portion directly coupled to the first end of the main supply tube inside of the second balloon and a second end portion connected to at least one of the plurality of micro-needles; and
a second supply tube having a first end portion directly coupled to the first end of the main supply tube inside of the second balloon and a second end portion connected to at least one of the plurality of micro-needles, the first end portion of the second supply tube being disposed proximate the first end portion of the first supply tube,
wherein expansion of the second balloon is configured to cause the plurality of micro-needles to penetrate through the outer surface of the first balloon after inflation of the first balloon.

2. The system of claim 1, wherein the outer surface of the first expandable balloon is configured to contact the target tissue within the pelvic region of the patient, the target tissue within the pelvic region being at least one of an inner surface of a bladder wall, an inner surface of a vaginal wall, an inner surface of an anal canal, an inner surface of a rectum, an inner surface of an anus, or an inner surface of a uterine wall.

3. The system of claim 1, wherein the first balloon comprises a material thickness and wherein one of the plurality of micro-needles comprise a length that is greater than the material thickness of the first balloon.

4. The system of claim 3, wherein the length of one of the plurality of micro-needles is at least as large as a combination of the thickness of the first balloon and a desired penetration depth into the target tissue.

5. The system of claim 1, wherein each of the plurality of micro-needles comprises a textured outer surface.

6. The system of claim 1, wherein at least one of the micro-needles includes a layer of material that covers an opening of the at least one micro-needle, the layer of material is biodegradable.

7. The system of claim 1, wherein at least one of the micro-needles includes a plurality of layers of material that cover an opening of the at least one of the micro-needle.

8. The system of claim 1, wherein a distal end portion of the second balloon is positioned within the first balloon.

9. The system of claim 1, wherein the first balloon includes an inner surface and an outer surface, the inner surface of the first balloon being separate from the outer surface of the second balloon.

10. A system for delivering a therapeutic material to a target tissue of a patient, the system comprising:
a first expandable balloon including an outer surface, the outer surface configured to contact the target tissue within a pelvic region of the patient;
a second expandable balloon at least partially positioned within the first balloon and separately inflatable from the first balloon, the second balloon including an inner surface, an outer surface, and a plurality of micro-needles disposed on the outer surface of the second balloon and extending outwardly from the outer surface of the second balloon;
a main supply tube that extends into the second balloon having a first end;
a first supply tube directly coupled to the first end of the main supply tube inside of the second balloon and a second supply tube directly coupled to the first end of the main supply tube inside of the second balloon, each of the first supply tube and the second supply tube being connected to at least one of the plurality of micro-needles,
wherein expansion of the second balloon is configured to cause the plurality of micro-needles to penetrate through the outer surface of the first balloon after inflation of the first balloon.

11. The system of claim 10, wherein the outer surface of the first expandable balloon is configured to contact the target tissue within the pelvic region of the patient, the target tissue within the pelvic region being at least one of an inner surface of a bladder wall, an inner surface of a vaginal wall, an inner surface of an anal canal, an inner surface of a rectum, an inner surface of an anus, or an inner surface of a uterine wall.

12. The system of claim 10, wherein the first balloon comprises a material thickness and wherein one of the plurality of micro-needles comprise a length that is greater than the material thickness of the first balloon.

13. The system of claim 10, wherein the length of one of the plurality of micro-needles is at least as large as a combination of the thickness of the first balloon and a desired penetration depth into the target tissue.

14. The system of claim 10, wherein each of the plurality of micro-needles comprises a textured outer surface.

15. The system of claim 10, wherein at least one of the micro-needles includes a layer of material that covers an opening of the at least one micro-needle, the layer of material is biodegradable.

16. The system of claim 10, wherein at least one of the micro-needles includes a plurality of layers of material that cover an opening of the at least one of the micro-needle.

17. The system of claim 10, wherein a distal end portion of the second balloon is positioned within the first balloon.

18. The system of claim 10, wherein the first balloon includes an inner surface and an outer surface, the inner surface of the first balloon being separate from the outer surface of the second balloon.

* * * * *